US007477366B2

(12) United States Patent
Clements et al.

(10) Patent No.: US 7,477,366 B2
(45) Date of Patent: Jan. 13, 2009

(54) CONTACT LENS BLISTER PACKAGES AND METHODS FOR AUTOMATED INSPECTION OF HYDRATED CONTACT LENSES (75) Inventors: Julie Clements, Southampton (GB); Steve Hope, Southampton (GB); Kevin Aldridge, Southampton (GB)

(73) Assignee: CooperVision International Holding Company, LP, St. Michael (BB)

( * ) Notice: Subject to any disclaimer, the term of this patent is extended or adjusted under 35 U.S.C. 154(b) by 125 days.

(21) Appl. No.: 11/567,765

(22) Filed: Dec. 7, 2006

(65) Prior Publication Data

US 2008/0137076 A1    Jun. 12, 2008

(51) Int. Cl.
G01B 9/00    (2006.01)
(52) U.S. Cl. .................................. 356/124; 206/5.1
(58) Field of Classification Search ................ 356/124, 356/244, 440; 206/5.1; 220/359.2
See application file for complete search history.

(56) References Cited

U.S. PATENT DOCUMENTS

| 4,691,820 | A |   | 9/1987  | Martinez  |
|-----------|---|---|---------|-----------|
| 5,443,152 | A |   | 8/1995  | Davis     |
| 5,467,868 | A |   | 11/1995 | Abrams    |
| 5,500,732 | A |   | 3/1996  | Ebel      |
| 5,515,964 | A |   | 5/1996  | Bauman    |
| 5,604,583 | A |   | 2/1997  | Byron     |
| 5,609,246 | A |   | 3/1997  | Borghorst |
| 5,620,088 | A |   | 4/1997  | Martin    |
| 5,633,504 | A |   | 5/1997  | Collins   |
| 5,704,468 | A |   | 1/1998  | Lust      |
| 5,722,536 | A |   | 3/1998  | Pierce    |
| 5,812,254 | A |   | 9/1998  | Ebel      |
| 5,818,573 | A |   | 10/1998 | Lafferty  |
| 5,943,436 | A |   | 8/1999  | Ebel et al. |
| 6,029,808 | A |   | 2/2000  | Peck      |
| 6,044,966 | A | * | 4/2000  | Haase .......................... 206/5.1 |
| 6,082,533 | A |   | 7/2000  | Smith     |
| 6,301,005 | B1 |  | 10/2001 | Epstein   |
| D458,023  | S |   | 6/2002  | Dzwill    |
| 6,398,018 | B1 |  | 6/2002  | Livesley  |
| 6,606,150 | B2 | * | 8/2003 | Bickert et al. ................ 356/124 |
| 6,614,516 | B2 |  | 9/2003  | Epstein   |

(Continued)

FOREIGN PATENT DOCUMENTS

EP    0 734 965 A1    10/1996

(Continued)

OTHER PUBLICATIONS

Extended European Search Report completed Mar. 14, 2008 and mailed Apr. 4, 2008 from corresponding European Patent Application No. 07254758.1, filed Dec. 7, 2007 (7 pages).

*Primary Examiner*—Kara E Geisel
(74) *Attorney, Agent, or Firm*—Klein, O'Neil & Singh, LLP (57) ABSTRACT A contact lens package includes a base member including a cavity dimensioned to accommodate contact lens and a liquid therein. The combination of the cavity, the contact lens, and the liquid cooperate to collimate partially collimated light directed toward a bottom surface of the cavity. The cavity can be sealed by attaching a removable sealing member to the base member around the cavity. Methods of inspecting ophthalmic lenses using the present packages are also described.

46 Claims, 4 Drawing Sheets

U.S. PATENT DOCUMENTS

| | | |
|---|---|---|
| 6,889,825 B2 | 5/2005 | Ichikawa |
| D511,893 S | 11/2005 | Chou |
| D512,217 S | 12/2005 | Chou |
| D520,867 S | 5/2006 | Chang |
| 7,057,186 B2 | 6/2006 | Ross, III |
| 7,079,239 B2 | 7/2006 | Bergendahl |
| 2003/0029736 A1* | 2/2003 | Phillips et al. ............... 206/5.1 |
| 2004/0214914 A1 | 10/2004 | Marmo |
| 2005/0218012 A1* | 10/2005 | Tanaka et al. ................ 206/5.1 |
| 2006/0213783 A1 | 9/2006 | Tokarski |
| 2006/0249403 A1 | 11/2006 | Newman |
| 2007/0034533 A1 | 2/2007 | Coldrey |

FOREIGN PATENT DOCUMENTS

| | | |
|---|---|---|
| EP | 1 092 645 A1 | 4/2001 |
| EP | 1 277 416 A2 | 1/2003 |

\* cited by examiner

CONTACT LENS BLISTER PACKAGES AND METHODS FOR AUTOMATED INSPECTION OF HYDRATED CONTACT LENSES

FIELD

The embodiments described herein relate to contact lens blister packages and methods of inspecting hydrated contact lenses using the blister packages.

BACKGROUND

The manufacture of ophthalmic lenses, such as contact lenses, includes inspecting lenses for defects and packaging the lenses in packages, among other things. In the production of large amounts of ophthalmic lenses, such as contact lenses, it is desirable to continue to develop new manufacturing components, systems, methods, and the like to reduce production time, to reduce production costs, and to increase productivity, among other things.

SUMMARY

A contact lens blister package, or a thermoplastic base member of a contact lens blister package, comprises a cavity dimensioned to accommodate a hydrated contact lens, and a flange outwardly extending from the cavity. When the package or base member is used to hold a hydrated contact lens during a lens inspection procedure, the cavity can be understood to be a light collimation cavity. Methods of inspecting contact lenses comprise using the blister packages or the thermoplastic base members.

DETAILED DESCRIPTION

Figure 1:
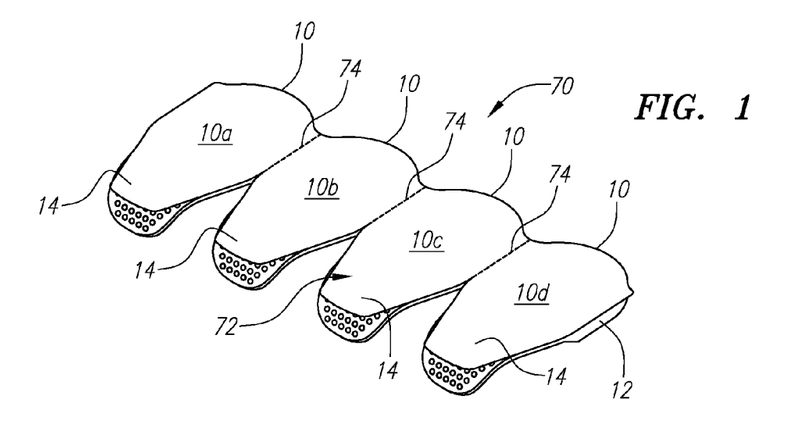
FIG. 1 is a perspective view of an array of sealed contact lens packages.

Referring to FIG. 1, an array 70 of a plurality of contact lens packages 10 is illustrated. The illustrated array 70 consists of four contact lens packages 10. Another array may consist of two contact lens packages. Another array may consist of three contact lens packages. Another array may consist of five contact lens packages. Additional arrays of packages may comprise more than five contact lens packages.

In the array 70, a contact lens package 10 is positioned adjacent at least one other contact lens package 10. For example, contact lens package 10a is adjacent one contact lens package 10b. In addition, contact lens package 10b and contact lens package 10c each are adjacent two contact lens packages. Contact lens package 10d is adjacent only one contact lens package 10c.

The present packages 10 are configured to contain contact lenses. Examples of contact lenses suitable for the present packages are hydrogel contact lenses. The hydrogel contact lenses can be silicone hydrogel contact lenses or non-silicone hydrogel contact lenses. A silicone hydrogel contact lens is a hydrogel contact lens that comprises a silicone component. Examples of silicone hydrogel contact lenses that can be packaged in the present packages include silicone hydrogel contact lenses having the following U.S. Adopted Names (USANs): lotrafilcon A, lotrafilcon B, balafilcon A, galyfilcon A, senofilcon A, and comfilcon A. A non-silicone hydrogel contact lens is a hydrogel contact lens that is free of a silicone component. Examples of non-silicone hydrogel contact lenses that can be packaged in the present packages include hydrogel contact lenses having the following USANs: omafilcon A, ocufilcon A, ocufilcon B, ocufilcon C, ocufilcon D, ocufilcon E, methafilcon A, methafilcon B, among others. Some of the contact lenses, either silicone hydrogel contact lenses or non-silicone hydrogel contact lenses, provided in the present packages include one or more comfort agents. Examples of comfort agents include wettability enhancing agents that enhance the wettability of the contact lenses so that the contact lenses remain comfortable to a lens wearer, even at the end of the day, such as after about 14 hours of continuously wearing the contact lenses. One example of a comfort agent is a surfactant. Examples of surfactants include poloxamers and poloxamines, among others. Another example of a comfort agent is a phosphoryl choline derivative (PC), such as methacrylate phosphoryl choline (MPC), 2-methacryloyloxyethyl phosphoryl choline (HEMA-PC), and the like, and combinations thereof. One example of contact lenses that include a phosphoryl choline derivative is available from CooperVision under the tradename Proclear. One example of a contact lens that is present in the present packages comprises a polymer comprising units of hydroxyethyl methacrylate, and a phosphoryl choline derivative.

Each of the contact lens packages 10 of the array of packages 70 comprises a base member 12 and a sealing member 14. Individual contact lens packages 10 are described below. In the array 70, each sealing member 14 can be understood to be a component of a sealing layer 72. The illustrated sealing layer 72 spans the entire array of contact lens packages 70. Individual packages 10 can be separated from the array 70 along the weakening lines 74. The weakening lines 74 are provided in proximity to the juxtaposition of two contact lens packages 10. The weakening lines 74 can be understood to be perforations in the sealing layer 72. In other embodiments, the weakening lines 74 may be formed without perforations, such as by providing a thinner portion, for example a relatively thinner continuous strip, of the sealing layer 72 in the desired location.

In the illustrated embodiment of FIG. 1, the individual packages 10 of the array 70 are attached to each other. For example, the packages 10 can include an attachment portion between two of the packages. The attachment portion can be an integral component of the array of packages, or it can be an additional securing element connecting two or more of the packages 10.

In the illustrated embodiment of FIG. 1, the base members 12 of the plurality of packages 10 are coupled together and are further coupled together by the single sealing layer 72. In other embodiments, the packages 10 may be coupled together only at the base members 12 and not by the sealing layer 72, or the packages 10 may be coupled together only by the sealing layer 72 and not by the base members 12.

Figure 2:
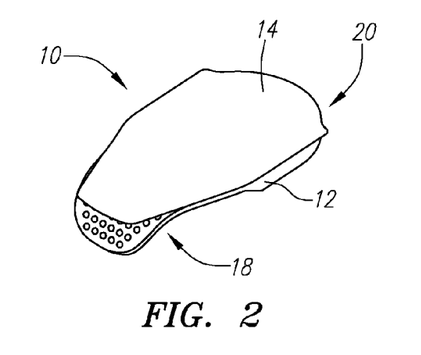
FIG. 2 is a perspective view of a single sealed package of the array of FIG. 1.
Figure 3:
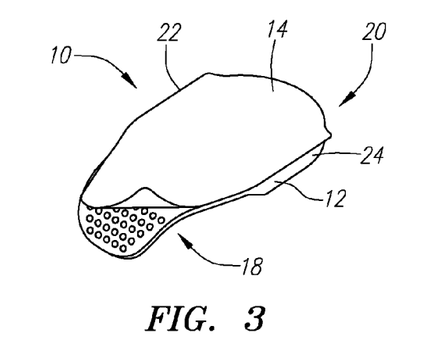
FIG. 3 is a perspective view of the package of FIG. 2 with the sealing member partially removed.

A sealed single contact lens package 10 is illustrated in FIG. 2. The contact lens package 10 comprises a base member 12 and a sealing member 14 coupled to the base member 12. FIG. 3 illustrates the contact lens package 10 of FIG. 2 with the sealing member 14 being partially removed. Thus, it can be understood that the sealing member 14 is a removable sealing member.

The sealing member 14 is coupled to a portion of the base member 12 to seal a contact lens in a cavity of the base member, as discussed herein. The sealing member 14, and also the sealing layer 72, can be formed from a variety of materials suitable for packaging of materials. Suitable materials should be able to be attached to a portion of the base member to maintain a contact lens contained in the cavity in a sterile condition. For example, the sealing member material should be able to be exposed to sterilizing conditions, such as autoclaving, gamma radiation, ultraviolet radiation, and the like without compromising the properties of the sealing member. The sealing member 14 may comprise one or more layers of materials, such as foils, plastics, and the like. The sealing member 14 may also include indicia, such as letters, numbers, graphics, and combinations thereof. In the illustrated embodiment of the present packages and arrays, the sealing member 14 is heat sealed to the base member 12. In other embodiments, adhesives or other suitable coupling mechanisms may be used to couple the sealing member 14 to the base member 12. Thus, the sealing member 14 provides a fluid impervious seal as well as a seal which prevents contamination of the sterilized contact lens and packaging liquid contained in the sealed cavity.

The base member 12, and also the contact lens package 10, comprise a proximal end region 18 and a distal end 20. The proximal end region 18 includes a grippable portion which can be held between two fingers of a person, such as a thumb and forefinger. For convenience, the proximal end region 18 can be understood to include a thumb grip. As shown in FIG. 3, the sealing member 14 can be removed by peeling the proximal portion of the sealing member 14 from the proximal end portion 18 of the base member 12. In the illustrated embodiment, the sealing member 14 is manually peeled by a person from the proximal end portion 18 towards the distal end 20 of the base member 12.

As shown in FIG. 3, the base member 12 comprises a first lateral side region 22 and an opposing second lateral side region 24. The first and second lateral side regions 22 and 24, respectively, extend from the proximal end region 18 towards the distal end 20 of the base member. The first and second lateral side regions, 22 and 24, respectively, can be parallel to each other, or can taper, such as by converging or diverging, towards the distal end 20.

Figure 4:
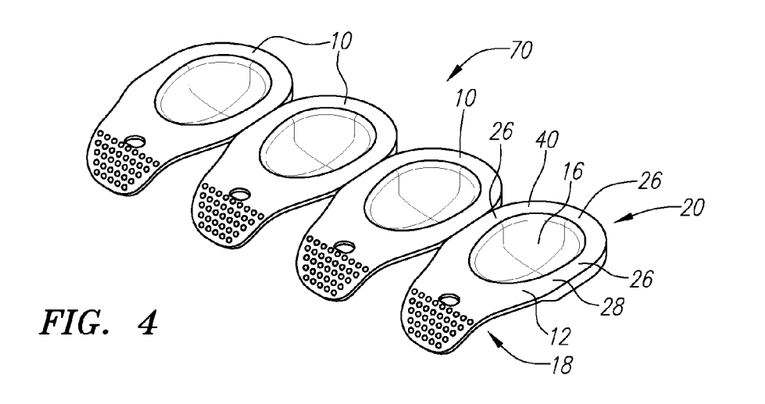
FIG. 4 is a perspective view of an array of unsealed contact lens packages.

An array 70 of contact lens packages 10 with the sealing layer 72 removed is illustrated in FIG. 4. For convenience, only one of the packages 10 of the array 70 of FIG. 4 is provided with reference numbers. It will be understood that the other packages 10 of the illustrated array 70 are identically structured. Each contact lens package 10 of the array 70 of FIG. 4 comprises a base member 12. The base member 12 comprises a cavity 16. The cavity 16 is located between proximal end region 18 and distal end 20. The base member 12 comprises a flange 26 extending outwardly from the cavity 16. The flange 26 comprises a flange top surface 28 and a flange bottom surface 30 (see FIG. 6).

In the illustrated embodiments presented herein, the flange 26 surrounds the perimeter of the cavity 26 and extends outwardly therefrom. The flange 26 includes a sealing area 40 to which the sealing member 14 can be attached to seal the cavity 16. The flange 26 can be understood to be a portion of the base member 12 extending outwardly from the cavity 16 to provide an attachment region for the sealing member 14. Near the proximal end of the cavity 16, the proximal portion of the flange 26 blends with the proximal end region 18 of the base member 12. The flange can have a width from about 1 mm to about 10 mm, for example, about 1 mm, about 2 mm, about 3 mm, about 4 mm, about 5 mm, about 6 mm, about 7 mm, about 8 mm, about 9 mm, or about 10 mm. Therefore, the sealing area 40 to which the sealing member 14 is attached can be understood to be a region from about 1 mm to about 10 mm extending from the edge of the cavity 16. Beyond the sealing area 40, the sealing member 14 is not attached or coupled to the base member 12. The sealing member 14 can then be grasped by a person at this non-attached region or regions and removed from the base member 12.

Figure 5:
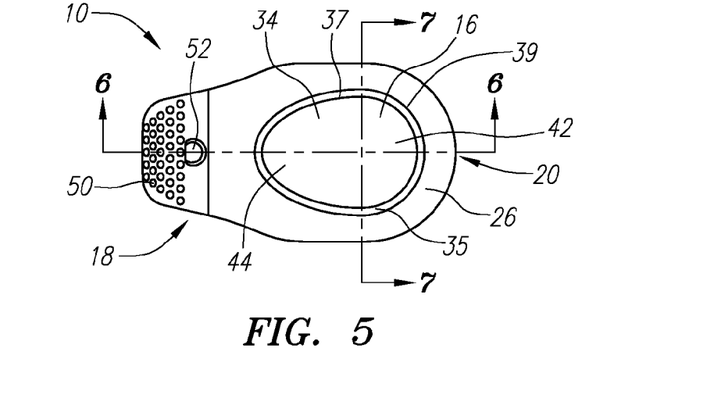
FIG. 5 is a top plan view of one unsealed contact lens package.
Figure 6:
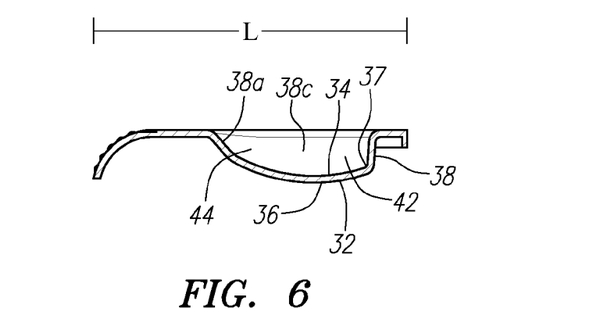
FIG. 6 is a sectional view of the package of FIG. 5 along line 6-6.
Figure 7:
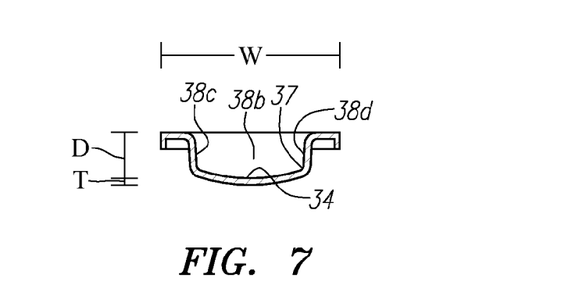
FIG. 7 is a sectional view of the package of FIG. 5 along line 7-7.

An individual unsealed contact lens package 10 is illustrated in FIG. 5. FIG. 6 is a sectional view along line 6-6 of FIG. 5, and FIG. 7 is a sectional view along line 7-7 of FIG. 5.

The cavity 16 of the base member 12 of the contact lens package 10 is defined by a bottom wall surface 34 and a cavity sidewall surface 35. As shown in FIG. 6, the bottom wall surface 34 is a surface of a cavity bottom wall 32. The bottom wall 32 can be understood to comprise a first bottom wall surface 34 (e.g., defining the bottom surface of the cavity 16) and a second opposing bottom wall surface 36. The bottom wall 32 has a thickness defined as the distance between the first bottom wall surface 34 and the second opposing bottom wall surface 36. The bottom wall surface 34 is surrounded by a bottom wall surface perimeter 37.

The base member 12 also includes a cavity sidewall 38. The cavity sidewall 38 includes the cavity sidewall surface 35 that helps define the cavity 16. The base member 12 can be understood to comprise a cavity 16 defined by a proximal sidewall portion 38a, a distal sidewall portion 38b, a first lateral sidewall portion 38c, and a second opposing lateral sidewall portion 38d (see FIGS. 6 and 7). The cavity 16 is surrounded by a cavity perimeter 39. The cavity perimeter 39 can be understood to be located at the junction of the upper end of the cavity sidewall surface 35 and the flange 26.

The cavity 16 comprises a distal cavity portion 42 and a proximal cavity portion 44, as shown in FIGS. 5 and 6. The distal cavity portion 42 comprises a spherical component, and the proximal cavity portion 44 comprises an aspherical component. For example, the bottom wall surface 34 of the distal cavity portion 42 can be a portion of a spherical surface, and the bottom wall surface of the proximal cavity portion 44 can be an aspherical surface.

Figure 8:
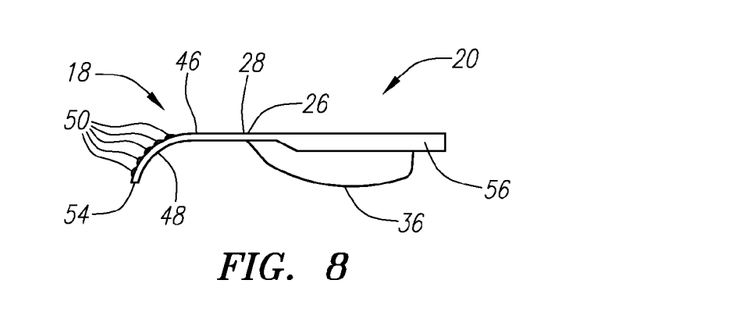
FIG. 8 is a side plan view of the package of FIG. 5.

As shown in FIG. 8, the proximal end portion 18 of the base member 12 comprises a first surface 46 and an opposing second surface 48. The first surface 46 is contiguous with the flange top surface 28. A plurality of bumps 50 are illustrated extending from the first surface 46. A recess or depression 52 is shown extending from the first surface 46 toward the second surface 48 (see FIGS. 5 and 8). The proximal portion 18 also comprises a proximal stabilizing portion 54 that in conjunction with bottom surface 36 stabilizes the base member 12 on a flat surface, such as a horizontal surface. A support rib 56 is illustrated in FIG. 8 extending downwardly from the flange top surface 28 and surrounding portions of the lateral sides and the distal end of the base member.

The base members of the present packages can be formed from a variety of materials. In certain embodiments, including the illustrated embodiments, the base members are plastic members. The base members can be made by any conventional technique. In the illustrated embodiment, the base members are injection molded elements. In other embodiments, the base members may be thermoformed. Thus, the present base members can be understood to comprise, consist essentially of, or consist entirely of, a thermoplastic material. In one embodiment, the base member is made of a polyolefin resin material, such as polypropylene.

When the base members of the present packages are used in a lens inspection method the base member material can transmit light such that a contact lens located in the base member cavity can be illuminated and an image of the lens can be obtained for inspection.

Figure 9:
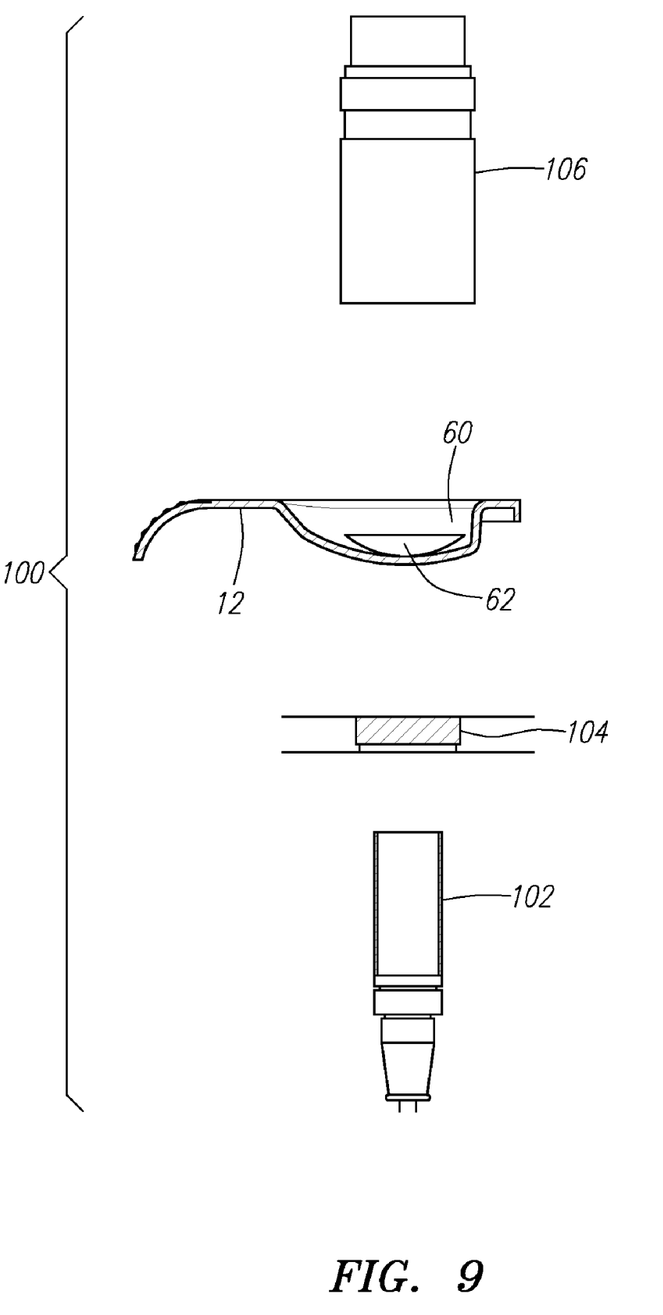
FIG. 9 is an illustration of a portion of an ophthalmic lens inspection system including the present packages.

An illustration of an ophthalmic lens inspection system 100 is shown in FIG. 9. The lens inspection system 100 comprises an illumination source 102, a lens 104, and a camera 106. A base member 12 of the present packages is located between the lens 104 and the camera 106. The base member 12 comprises a liquid 60 in the cavity and an ophthalmic lens 62 in the liquid. As described herein, the ophthalmic lens 62 can be a contact lens, such as a hydrogel contact lens.

Figure 10:
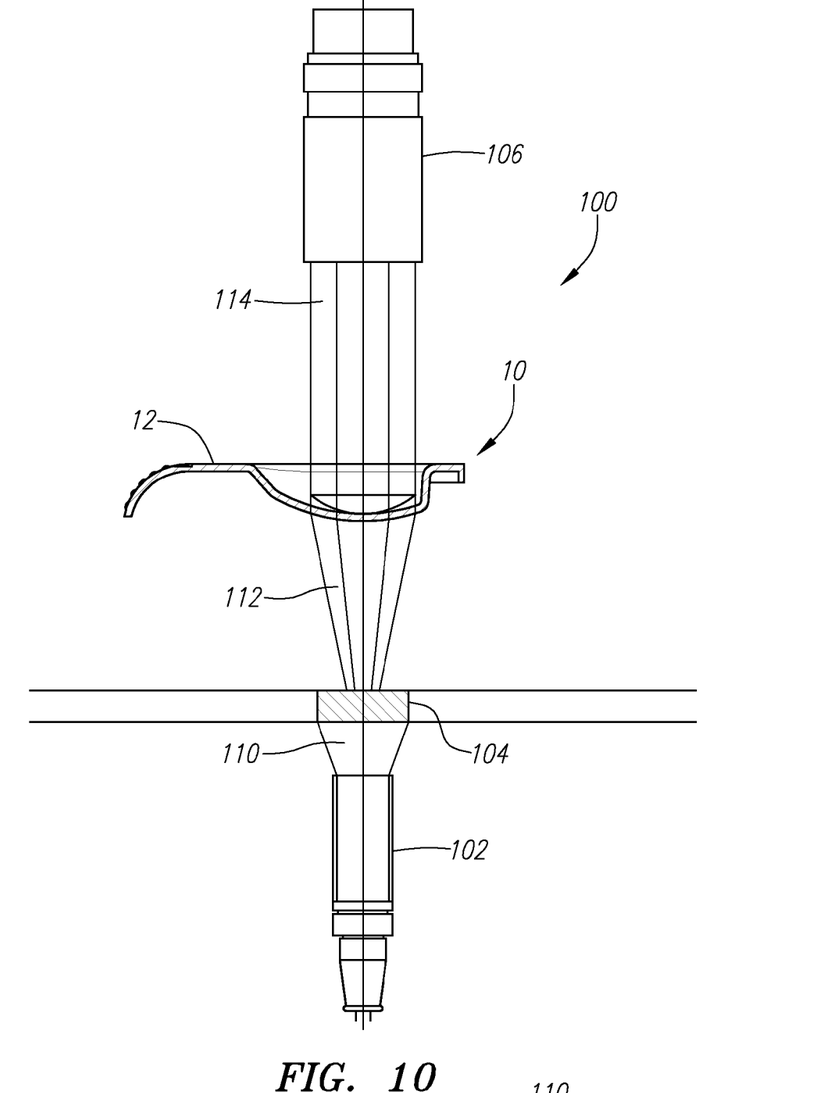
FIG. 10 is an illustration of a portion of an ophthalmic lens inspection system in which partially collimated light is collimated by the bottom wall of the package cavity, the ophthalmic lens, and the liquid present in the cavity.
Figure 11:
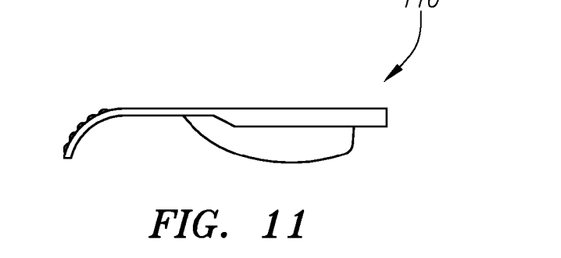
FIG. 11 is a side plan view of another contact lens package.

As shown in FIG. 10, the illumination source 102 provides diffuse light 110 that is directed toward lens 104. In the illustrated embodiment, the illumination source 102 is a light emitting diode (LED). The diffuse light 110 is partially collimated by lens 104. Therefore, lens 104 can be understood to be a light collimating lens that is effective in converting diffuse light 110 to partially collimated light 112. The partially collimated light 112 is directed to the base member 12 of the contact lens package 10. The combination of the cavity bottom wall 34, the ophthalmic lens 62, and the liquid 60 cooperate to fully collimate the light as the light is directed towards the camera 106. Thus, the camera 106 receives parallel rays of light 114 and is able to obtain and produce a uniform bright field image of the ophthalmic lens. The image of the ophthalmic lens can be inspected for defects. If no defects are detected, the sealing member can be sealed to the base member. The sealed contact lens package can then be sterilized and distributed from the lens manufacturer.

In view of the present disclosure, an embodiment of the present contact lens blister packages comprises a thermoplastic base member. The thermoplastic base member comprises a light collimation cavity. The light collimation cavity can be understood to be a cavity that cooperates with liquid present in the cavity and a contact lens in the liquid to collimate partially collimated light to provide a uniform bright field image of the contact lens during an inspection procedure. The light collimation cavity is dimensioned, such as sized and shaped, to accommodate a hydrated contact lens in a liquid composition present in the cavity. The base member also comprises a flange extending outwardly from the light collimation cavity. The flange includes a sealing area to which a sealing member can be attached to seal the contact lens and liquid composition in the cavity.

The light collimation cavity of these embodiments may comprise a curved bottom surface having a bottom surface perimeter, as described herein. The cavity may also comprise an upwardly extending cavity sidewall surface extending from the bottom surface perimeter to an upper perimeter cavity edge. The upper perimeter cavity edge can be understood to define a light collimation cavity perimeter. The light collimation cavity perimeter is greater than the bottom surface perimeter. In other embodiments, the light collimation cavity perimeter is equal to the bottom surface perimeter.

In certain embodiments, the curved light collimation cavity bottom surface has a radius of curvature at least twice as large as the base curve of a hydrated contact lens that is to be placed in the cavity. For example, the radius of curvature can be at least 200% larger, at least 300% larger, or at least 400% larger than the base curve of the hydrated contact lens. For example, if a hydrated contact lens has a base curve of about 8 mm, the radius of curvature of the cavity bottom surface can be at least 16 mm, at least 24 mm, or at least 32 mm. In certain embodiments, the radius of curvature of the cavity bottom surface is from about 15 mm to about 26 mm. The radius of curvature can be identical along the length and along the width of the cavity, or they can be different. For example, in at least one embodiment, the cavity bottom surface has a radius of curvature from about 25 mm to about 26 mm along the length of the bottom surface, and an identical radius of curvature along the width of the bottom surface.

Some embodiments of the present contact lens blister packages comprise a cavity sidewall that extends from the planar flange region toward a central region of the light collimation cavity at an angle from about 80° to about 90°. In certain embodiments, the angle is less than 90°. Orienting the sidewall or a portion thereof at these angles can be useful to provide sufficient space to accommodate a hydrated contact lens. It can be understood that the entire sidewall does not need to be oriented between about 80° and about 90°. For example, along the proximal portion of the cavity, as discussed herein, the sidewall can have a more shallow slope, which may be useful in facilitating removal of the contact lens from the cavity.

The base member of the present blister packages may also comprise a proximal end region having a thumb grip region, an opposing distal end region, a first side region extending from the proximal end region to the opposing distal end region, and an opposing second side region extending from the proximal end region to the opposing distal end region and substantially opposing the first side region. The light collimation cavity is located between the proximal end region and the distal end region and between the first and second side regions.

As shown in FIG. 6 and FIG. 7, the base member can have a length L extending from the proximal end region to the opposing distal end region. The base member can also have a width W extending from the first side region to the opposing second side region. The light collimation cavity has a cavity length that is parallel to the base member length, and has a cavity width that is parallel to the base member width. In certain embodiments, including the illustrated embodiments, the cavity length is greater than the cavity width. For example, the cavity width can be from about 60% to about 90% of the cavity length. In certain embodiments, the maximum cavity width is about 80% of the maximum cavity length.

As described herein, the sidewall surface of the cavity can vary in slope. For example, the illustrated embodiments of the present packages comprise a cavity having a cavity sidewall that has a proximal sidewall portion that has a shallower slope compared to a more distal portion of the cavity sidewall. The configuration of the cavity including the shape of the bottom surface and sidewall surface can be useful in maintaining the lens in a desired position within the cavity, such as during inspection, and can be useful in facilitating removal of the contact lens from the cavity onto a person's finger. In view of the disclosure herein, some embodiments of the present light collimation cavities can be understood to have a cavity perimeter that is substantially egg-shaped with the narrowest portion of the perimeter being located closer to the proximal end region of the base member than to the opposing distal end of the base member. Other embodiments may include other shaped perimeters, including elliptical, ovoid, tear shaped, and even circular, if desired. In certain embodiments, the contact lenses remain substantially centered in the cavity when the package is placed on a horizontal surface with the cavity opening facing up.

Depending on the state of the present blister packages, certain embodiments comprise a liquid located in the light collimation cavity and a contact lens fully immersed in the liquid. For example, if the blister package is at a lens inspection station of a manufacturing line, at a sealing station of a manufacturing line, at a sterilization station of a manufacturing line, or at a distribution center or other storage location, including physician's offices or lens wearer's residences, the blister package comprises a liquid in the cavity and a contact lens in the liquid. The liquid can be understood to be a contact lens packaging solution. Examples of contact lens packaging solutions include saline solutions, such as buffered saline solutions. Some specific examples include borate buffered solutions, phosphate buffered solutions, bicarbonate buffered solutions, and the like. In certain embodiments, the liquid in the cavity includes a surfactant, such as non-ionic surfactants. Examples of surfactants that may included in the present packaging liquids include poloxamers, publicly available as Pluronics, and poloxamines, publicly available as Tetronics. Other surfactants include polysorbates, such as TWEENS, including TWEEN-80. The amount of surfactant can range from about 0.005 weight percent to about 2.0 weight percent. The liquid can additionally or alternatively include other agents, such as polyvinyl alcohol; polyvinyl pyrrolidone; cellulose derivatives, such as carboxymethyl cellulose, hydroxypropyl methyl cellulose, hydroxyethyl cellulose, methyl cellulose, and methyl ether cellulose; and polyethylene glycol.

Another embodiment of a contact lens blister package comprises a thermoplastic base member that comprises a light collimation cavity defined by a bottom wall surface. The bottom wall surface has a perimeter, and the cavity is further defined by a sidewall surface extending from the bottom wall surface perimeter upwardly toward a flange extending outwardly from the cavity. In this embodiment, the cavity has a maximum length of about 25 mm and a maximum width of about 20 mm, and the bottom wall surface has a radius of curvature from about 15 mm to about 26 mm.

The bottom wall surface of this embodiment may be a surface of a cavity bottom wall, as described herein. In certain embodiments, the cavity bottom wall has a thickness less than 1 mm. In further embodiments, the thickness of the bottom wall is about 0.8 mm. The thickness of the bottom wall is substantially constant across the entire bottom wall in certain embodiments. For example, the thickness of the bottom wall may vary from 0.75 mm to 0.85 mm.

The cavities of the present packages are dimensioned to accommodate a hydrated contact lens. Thus, a cavity can have a maximum depth so that a hydrated contact lens can be fully immersed in a liquid composition present in the cavity. In certain embodiments, the cavity has a maximum depth less than 9 mm. For example, the cavity can have a maximum depth of about 6 mm, about 7 mm, about 8 mm, or about 9 mm. In at least one embodiment, the cavity has a maximum depth of about 7.0 mm.

Certain embodiments of the blister package comprise a cavity having a sidewall surface that comprises a proximal sidewall portion, a distal sidewall portion, a first lateral sidewall portion, and a second lateral sidewall portion opposing the first lateral sidewall portion. One or more of the distal sidewall portion, the first lateral sidewall portion, and the second lateral sidewall portion is oriented at an angle of about 5 degrees from a straight line extending from the bottom wall surface and perpendicular to a top surface of the flange.

The base member of the present packages may also comprise a proximal end region that is grippable by fingers of a person, such as a thumb grip region as described herein. In certain embodiments, the proximal end region comprises a first surface that is continuous with a top surface of the flange, and a plurality of raised bumps extending from the first surface. In certain embodiments, such as the illustrated embodiments, the proximal end region may comprise a gate recess projecting from the first surface. In additional embodiments, the proximal end region may comprise indicia, such as numbers, letters, graphics, and combinations thereof. For example, a thumb grip region may include the tradename of the contact lens located in the cavity. The indicia can be provided as ink on the thumb grip region, or can be raised structures similar to the raised bumps and produced during the manufacture of the base member.

In certain embodiments, the flange of the base member has a maximum width of about 3 mm. The base member may also have a maximum width of about 27 mm, a maximum length of about 46 mm.

Another embodiment presented herein is a thermoplastic base member of a contact lens blister package. The base member has a length and a width, as described herein. The base member comprises a cavity having a bottom wall surface and a sidewall surface extending perimetrically from the bottom wall surface. The base member also comprises a flange outwardly extending from the cavity. The bottom wall surface of the cavity has a radius of curvature from about 15 mm to about 26 mm along the length of the base member and along the width of the base member. In other words, the radius of curvature of the bottom wall surface is equal in both directions (e.g., along the length and along the width of the base member). In certain embodiments, the bottom wall surface is a surface of a bottom wall having a thickness of about 0.8 mm. In additional embodiments, the radius of curvature is from about 25 mm to about 26 mm. In further embodiments, the cavity has a maximum depth of about 7 mm. The base member may comprise a proximal finger grippable region, and the cavity has a proximal end with a width that is less than the distal end width of the cavity. For example, the cavity can have the configuration as shown in FIG. 5. In addition, the base member can further comprise a support rib depending from the flange and spaced apart from the cavity, as described herein.

In addition, the contact lenses that may be present in the cavity liquid include silicone hydrogel contact lenses and non-silicone hydrogel contact lenses, as described herein. In certain embodiments, the present packages comprise a daily disposable contact lens, such as a contact lens that is intended to be worn for about 10-16 hours and then discarded.

The present packages may also comprise a sealing member that is removably attached to the sealing area of the flange. The attached sealing member forms a sealed enclosure containing the liquid and contact lens. In certain embodiments, the sealing member is attached to the base member after a lens inspection procedure. Thus, such embodiments may be understood to be post-inspected contact lens blister packages.

As described herein, the base members of the present packages can be made from a variety of thermoplastic materials. In certain embodiments, the base member is an injection molded polyolefin material. For example, some of the base members, including the illustrated base members, are formed from polypropylene.

As shown in the drawings, the present blister packages can be coupled together to form an array of contact lens blister packages. The present arrays can consist of two, three, four, five, six, or more blister packages arranged in a strip, as described herein.

One specific example of a contact lens blister package comprises an injection molded polypropylene base member comprising a cavity and an outwardly extending flange. The cavity has an oblong configuration when viewed from the top, as shown in FIG. 5. The cavity has a maximum length of about 25 mm to about 26 mm, a maximum width of about 20 mm, and a maximum depth of about 7 mm. The bottom surface of the cavity has a single radius of curvature between about 25 mm and about 26 mm in both the X and Y directions (e.g. along the length and width of the cavity). The wall thickness of the base member is about 0.80 mm. The total length of the base member is about 46 mm, and the total width is about 26 to about 27 mm. The sealing area width around the cavity is about 3.0 mm. The proximal end region of the base member comprises a thumb grip with a plurality of raised bumps and a gate recess formed from an injection molding procedure. The proximal portion of the cavity has a sloped sidewall oriented at an angle of about 30° relative to the top surface of the flange.

The present packages and arrays of packages can be made using conventional methods known to persons of ordinary skill in the art. For example, the base members of the packages and packages arrays can be injection molded from thermoplastic resin materials in an injection molding machine. A liquid, such as a contact lens packaging solution, can be dispensed in the cavity of the base member, and a contact lens can be inserted into the liquid. Alternatively, a contact lens can be placed into the cavity, and a liquid can then be dispensed in the cavity. The sealing member can then be applied to the sealing area of the base member to seal the liquid and contact lens in the cavity. The sealed package containing the hydrated contact lens can then be sterilized and prepared for distribution.

Typically, before the sealing member is applied to the base member, the lens located in the cavity can be inspected. The inspection can be manual or automated. Automated inspection methods are beneficial in the production of large amounts of contact lenses. Thus, a method of inspecting a hydrated contact lens comprises providing a contact lens in a liquid present in a cavity of the packages described herein. Partially collimated light is directed through the cavity, the liquid, and the contact lens to produce fully collimated light. A bright field image of the contact lens is obtained using a camera that receives the fully collimated light. The image can then be transferred to a computer for processing, such as by running one or more lens inspection algorithms using the image. The methods can be practiced serially or in parallel. For example, in certain embodiments, such as when arrays of blister packages are used in the production of contact lenses, the method is performed simultaneously on a plurality of packages. By producing uniform illumination of the contact lens based on the unique bottom surface configuration of the cavity, the lens edge and lens defects can be high-lighted by the collimated light.

Various additional features of the blister packages and base members can be provided. For example, embodiments of the present packages and base members may comprise a cavity having a non-planar proximal sidewall portion. A single package or base member may be understood to comprise only one cavity, for example, a single package may comprise a base member that consists of a cavity, a flange, and a thumbgrip region. The package may be free of markings that indicate the diameter of the contact lens contained therein. The package or base member may be free of lateral opposing indentations for grasping between a thumb and index finger. The cavity of the package or base member can be free of raised ribs extending into the cavity from a cavity bottom surface. In addition, the radius of curvature of the bottom surface of the cavity can be much greater than 12 mm, as described herein. The cavity can be understood to be free of an inwardly extending contact lens retaining lip extending from the flange region towards the center of the cavity. In addition, the cavity can be understood to be a single chamber for storing the contact lens. The cavity bottom wall can be understood to be non-invertible. In certain embodiments, the present packages and base members comprise a non-semi-circular cavity, a non-rectangular flange, or both. Embodiments of the present packages are free of grooves to receive peripheral portions of the flexible cover sheet. Some embodiments of the present packages and base members can be understood to be free of a plurality of interlockable or interengageable legs. The cavities of the packages and base members can be understood to be free of a convex mold portion extending upwardly from the bottom surface of the cavity. As discussed herein, embodiments of the present packages and base members can have a cavity with a bottom wall thickness greater than 0.75 mm. In addition, embodiments can have cavities that contain more than 0.75 ml of a packaging solution.

Although the disclosure herein refers to certain specific embodiments, it is to be understood that these embodiments are presented by way of example and not by way of limitation. Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment disclosed herein. The intent of the foregoing detailed description, although discussing exemplary embodiments, is to be construed to cover all modifications, alternatives, and equivalents of the embodiments described in the present description and claims.

What is claimed is:

1. A contact lens blister package, comprising:
    a thermosplastic base member comprising a light collimation cavity having a liquid and a contact lens present in the light collimation cavity, and a flange extending outwardly from the light collimation cavity, the flange including a sealing area to which a sealing member can be attached to seal the contact lens and the liquid in the cavity;
    wherein the light collimation cavity comprises a bottom surface having a bottom surface perimeter, and an upwardly extending cavity sidewall surface extending form the bottom surface perimeter to an upper perimeter cavity edge defining a light collimation cavity perimeter, and
    wherein the light collimation cavity perimeter is greater than the bottom surface perimeter; and wherein the light collimation cavity bottom surface has a radius of curvature at least 200% larger than a base curve of the contact lens.

2. The package of claim 1, wherein the cavity sidewall extends from the planar flange region toward a central region of the light collimation cavity at an angle from about 80° to less than 90°.

3. The package of claim 2, wherein the base member further comprises a proximal end region having a thumb grip region, an opposing distal end region substantially opposing the proximal end region, a first side region extending from the proximal end region to the opposing distal end region, and an opposing second side region extending from the proximal end region to the opposing distal end region and substantially opposing the first side region, wherein the light collimation cavity is located between the proximal end region and the opposing distal end region, and between the first side region and the opposing second side region.

4. The package of claim 3, wherein the base member has a length extending form the proximal end region to the opposing distal end region, and a width extending from the first side region to the opposing second side region, and the light collimation cavity has a cavity length parallel to the base member length and has a cavity width parallel to the base member width, wherein the cavity length is greater than the cavity width.

5. The package of claim 4, wherein the cavity sidewall has a proximal sidewall portion positioned closer to the proximal end region of the base member than to the opposing distal end region of the base member, the proximal sidewall portion having a shallower slope compared to a more distal portion of the cavity sidewall.

6. The package of the claim 5, wherein the light collimation cavity perimeter is substantially egg-shaped with the narrowest portion of the perimeter being located closer to the proximal end region of the base member than to the opposing distal end region of the base member.

7. The package of claim 1, wherein the contact lens is fully immersed in the liquid.

8. The package of claim 1, wherein the liquid is a buffered saline solution.

9. The package of claim 1, wherein the contact lens is a silicone hydrogel contact lens.

10. The package of claim 1, wherein the contact lens is a daily disposable contact lens.

11. The package of claim 1, wherein the contact lens remains substantially centered in the cavity when the package is placed on a horizontal surface with the cavity opening facing up.

12. The package of claim 1, wherein the liquid includes a surfactant.

13. The package of claim 1, further comprising a sealing member removable attached to the sealing area of the flange thereby forming a sealed enclosure containing the liquid and contact lens.

14. The package of claim 1, wherein the base member is an injection molded polyolefin material.

15. The package of claim 1 coupled to tat least one other identical package to form an array of lens packages.

16. A contact lens blister package, comprising:
a thermoplastic base member comprising a liquid and a contact lens located in a light collimation cavity defined by a bottom wall surface having a perimeter, and a sidewall surface extending from the bottom wall surface perimeter upwardly toward a flange extending outwardly from the cavity,
wherein the cavity has a maximum length of about 25 mm and a maximum width of about 20 mm, and the bottom wall surface has a radius of curvature of at least 200% larger than a base curve of the contact lens.

17. The package of claim 16, wherein the bottom wall surface is a surface of a cavity bottom wall, and the cavity bottom wall has a thickness less than 1 mm.

18. The package of claim 17, wherein the cavity bottom wall thickness is about 0.8 mm.

19. The package of claim 16, wherein the cavity has a maximum depth of about 7.0 mm.

20. The package of claim 16, wherein the sidewall surface comprises a proximal sidewall portion, a distal sidewall portion, a first lateral sidewall portion, and a second lateral sidewall portion opposing the first lateral sidewall portion, at least one of the distal sidewall portion, the first lateral sidewall portion, and the second lateral sidewall portion is oriented at an angle of about 5 degrees from a straight line extending from, the bottom wall surface and perpendicular to a top surface of the flange.

21. The package of claim 16, wherein the base member further comprises a proximal end region grippable by fingers of a person, the proximal end region comprising a first surface continuous with a top surface of the flange, and a plurality of raised bumps extending form the first surface.

22. The package of claim 21, wherein the proximal end region further comprises a gate recess projecting from the first surface.

23. The package of claim 21, wherein the proximal end region further comprises indicia selected from the group consisting of numbers, letters, graphics, and combinations thereof.

24. The package of claim 16, wherein, the flange has a maximum width of about 3 mm.

25. The package of claim 16, wherein the base member has a maximum width of about 27 mm, and a maximum length of about 46 mm.

26. The package of claim 16, wherein the contact lens is fully immersed in the liquid.

27. The package of claim 26, wherein the liquid is a buffered saline solution.

28. The package of claim 26, wherein the liquid comprises a surfactant.

29. The package of claim 26, wherein the contact lens is a silicone hydrogel contact lens.

30. The package of claim 16, wherein the contact lens is a silicone hydrogel contact lens.

31. The package of claim 16, wherein the contact lens is a daily disposable contact lens.

32. The package of claim 16, wherein the contact lens comprises a polymer of hydroxyethyl methacrylate and a phosphoryl choline derivative.

33. The package of claim 16, further comprising a removable sealing member coupled to the flange.

34. The package of claim 16 coupled to at least one identical package to form an array of lens packages.

35. The package of claim 34 which is present in an array of three lens packages.

36. The package of claim 34 which is present in an array of the five lens packages.

37. A contact lens blister package, comprising a thermoplastic base member having a length and a width, the base member comprising:
only one cavity to retain a liquid composition, the only one cavity being noncircular, having a bottom wall surface and a sidewall surface extending perimetrically from the bottom wall surface;
a liquid and a contact lens in the cavity; and
a flange outwardly extending from the only one cavity,
wherein the bottom wall surface has a radius of curvature from about 15 mm to about 26 mm along the length of the base member and along the width of the base member, and wherein the radius of curvature is about 200% greater than a base curve of the contact lens, and the bottom wall surface is configured to collimate light.

38. The contact lens blister package of claim 37, wherein the bottom wall surface is a surface of a bottom wall having a thickness of about 0.8 mm.

39. The contact lens blister package of claim 38, wherein the radius of curvature is from about 25 mm to about 26 mm.

40. The contact lens blister package of claim 38, wherein the cavity has a maximum depth of about 7 mm.

41. The contact lens blister package of claim 38, further comprising a proximal finger grippable region, and wherein the cavity comprises a proximal end in proximity of the proximal finger grippable region, and an opposing distal end, the proximal end having a width that is less than a width of the distal end.

42. The contact lens blister package of claim 37, wherein the contact lens is a silicone hydrogel contact lens.

43. The contact lens blister package 37, further comprising a support rib depending from the flange and spaced apart from the cavity.

44. A method of inspecting a hydrated contact lens, comprising:

providing a contact lens in a liquid present in a light collimation cavity of a contact lens blister package, wherein the light collimation cavity has a bottom wall surface having a radius of curvature from about 15 mm to about 26 mm along a length of the cavity and along a width of the cavity;

directing partially collimated light through the light collimation cavity, and liquid and contact lens provided therein, to produce fully collimated light; and obtaining a bright field image of the contact lens using a camera receiving the fully collimated light.

45. The method of claim 44, wherein the method is simultaneously performed on a plurality of contact lens packages.

46. The package of claim 37, further comprising a removable sealing member coupled to the flange.

* * * * *

UNITED STATES PATENT AND TRADEMARK OFFICE
CERTIFICATE OF CORRECTION

PATENT NO. : 7,477,366 B2  Page 1 of 1
APPLICATION NO. : 11/567765
DATED : January 13, 2009
INVENTOR(S) : Julie Clements et al.

It is certified that error appears in the above-identified patent and that said Letters Patent is hereby corrected as shown below:

On the Title page, in item (74), in "Attorney, Agent, or Firm", in column 2, line 1, delete "O'Neil" and insert -- O'Neill --, therefor.

In column 10, line 42, in Claim 1, delete "thermosplastic" and insert -- thermoplastic --, therefor.

In column 10, line 52, in Claim 1, delete "form" and insert -- from --, therefor.

In column 11, line 9, in Claim 4, delete "form" and insert -- from --, therefor.

In column 11, line 42, in Claim 13, delete "removable" and insert -- removably --, therefor.

In column 11, line 48, in Claim 15, delete "tat" and insert -- at --, therefor.

In column 11, line 51, in Claim 16, delete "thermosplastic" and insert -- thermoplastic --, therefor.

In column 12, line 8, in Claim 20, delete "from," and insert -- from --, therefor.

In column 12, line 14, in Claim 21, delete "from," and insert -- from --, therefor.

In column 12, line 49, in Claim 36, before "five" delete "the".

In column 13, line 13, in Claim 43, delete "package 37," and insert -- package of claim 37, --, therefor.

Signed and Sealed this

Fifteenth Day of June, 2010

David J. Kappos
*Director of the United States Patent and Trademark Office*